(12) United States Patent
Mokaya et al.

(10) Patent No.: US 10,130,298 B2
(45) Date of Patent: Nov. 20, 2018

(54) MUSCULOSKELETAL ACTIVITY RECOGNITION SYSTEM AND METHOD

(71) Applicant: Carnegie Mellon University, Pittsburgh, PA (US)

(72) Inventors: Frank Mokaya, Pittsburgh, PA (US); Pei Zhang, Mountain View, CA (US)

(73) Assignee: CARNEGIE MELLON UNIVERSITY, Pittsburgh, PA (US)

(*) Notice: Subject to any disclaimer, the term of this patent is extended or adjusted under 35 U.S.C. 154(b) by 875 days.

(21) Appl. No.: 14/390,419

(22) PCT Filed: Mar. 15, 2013

(86) PCT No.: PCT/US2013/032595
§ 371 (c)(1),
(2) Date: Oct. 3, 2014

(87) PCT Pub. No.: WO2013/151770
PCT Pub. Date: Oct. 10, 2013

(65) Prior Publication Data
US 2015/0045699 A1 Feb. 12, 2015

Related U.S. Application Data

(60) Provisional application No. 61/686,319, filed on Apr. 3, 2012.

(51) Int. Cl.
*A61B 5/00* (2006.01)
*A61B 5/11* (2006.01)
*A61B 5/22* (2006.01)

(52) U.S. Cl.
CPC .......... *A61B 5/4519* (2013.01); *A61B 5/0004* (2013.01); *A61B 5/0024* (2013.01);
(Continued)

(58) Field of Classification Search
CPC .......................... A61B 5/4519; A61B 5/0004
(Continued)

(56) References Cited

U.S. PATENT DOCUMENTS 7,027,953 B2   4/2006   Klein
7,219,033 B2   5/2007   Kolen
(Continued)

FOREIGN PATENT DOCUMENTS

WO   WO 2012/006549 A2   1/2012

OTHER PUBLICATIONS

Coyle et al., "Extracting Features for a Brain-Computer Interface by Self-Organising Fuzzy Neural Network-based Time Series Prediction," Proceedings of the 26th Annual International Conference of the IEEE EMBS, San Francisco, CA, USA, Sep. 1-5, 2004, pp. 4371-4374.
(Continued)

*Primary Examiner* — Daniel Cerioni
*Assistant Examiner* — Yasmeen S Warsi
(74) *Attorney, Agent, or Firm* — K&L Gates LLP

(57) ABSTRACT

A muscle activity and skeletal monitoring system and method are disclosed. A network of at least two distributed inertial sensor nodes are configured to communicate with each other over a first interface. Each of the inertial sensor nodes comprises at least one sensor configured to sense muscle vibrations and monitor body motion. A muscle activity recognition and motion tracking and visualization methods also are disclosed.

15 Claims, 9 Drawing Sheets

(52) U.S. Cl.
CPC .......... *A61B 5/1101* (2013.01); *A61B 5/1107* (2013.01); *A61B 5/1126* (2013.01); *A61B 5/224* (2013.01); *A61B 5/7203* (2013.01); *A61B 5/725* (2013.01); *A61B 5/7257* (2013.01); *A61B 5/7267* (2013.01); *A61B 5/7278* (2013.01); *A61B 5/7425* (2013.01); *A61B 2562/0219* (2013.01)

(58) Field of Classification Search
USPC ........................................ 600/587, 595, 554
See application file for complete search history.

(56) References Cited

U.S. PATENT DOCUMENTS

| | | | |
|---|---|---|---|
| 2010/0222711 | A1 | 9/2010 | Lajeunesse |
| 2011/0196262 | A1* | 8/2011 | McLeod .............. A61B 5/0053 600/587 |

OTHER PUBLICATIONS

Murphy et al., "Micro Electro Mechanical Systems Based Sensor for Mechanomyography," Biosignal, 2008.
Amft et al., "Sensing Muscle Activities with Body-Worn Sensors", Proceedings of the International Workshop on Wearable and Implantable Body Sensor Networks, IEEE Computer Society, 2006, 4 pages.
Ghasemzadeh et al., "A Body Sensor Network with Electromyogram and Inertial Sensors: Multimodal Interpretation of Muscular Activities", IEEE Transactions on Information Technology in Biomedicine, Mar. 2010, vol. 14, No. 2: pp. 198-206.
Hall et al., "The WEKA Data Mining Software: An Update", SIGKDD Explorations, 2009, vol. 11, Issue 1, pp. 10-18.
Ogris et al., "Using FSR based muscule activity monitoring to recognize manipulative arm gestures", 11th IEEE International Symposium on Wearable Computers, Oct. 2007, 4 pages.
Tarata, M. T., "Mechanomyography versus Electromyography, in monitoring the muscular fatigue", BioMedical Engineering Online, Feb. 11, 2003, pp. 1-10.
Wood, J. and D. Barry, "Time-Frequency Analysis of Skeletal Muscle and Cardiac Vibrations", Proceedings of the IEEE, Sep. 1996, vol. 84 No. 9, 1281-1294.
Analog Devices, ADXL345 Digital Accelerometer Data Sheet, Rev. D, Feb. 2013, Analog Devices, Inc., 40 pages.
3-Axis Digital Compass IC HMC5883L Data Sheet, Rev. E, Honeywell International Inc., Feb. 2013, 20 pages.
InvenSense Inc. ITG-3200 Product Specification data sheet, Revision 1.3, May 5, 2010, 39 pages.
Atmel Corporation, ATmega128RFA1 8-bit AVR ® Microcontroller with Low Power 2.4GHz Transceiver for ZigBee and IEEE 802.15.4 data sheet, Aug. 2011, 560 pages.
8-bit AVR® Microcontroller with 32K Bytes In-System Programmable Flash, ATmega328P, Automotive, Preliminary, Atmel Corporation, 7810A-AVR, Nov. 2009, 345 pages.
MRF24WB0MA/MRF24WB0MB Data Sheet, 2.4 GHz, IEEE Std. 802.11b™RF Transceiver Module, Microchip Technology Inc., May 2, 2011, 37 pages.
Long et al., "Single-Accelerometer-Based Daily Physical Activity Classification", 31st Annual International Conference of the IEEE EMBS, Minneapolis, Minnesota, USA, Sep. 2-6, 2009, pp. 6107-6110.
Bao et al., "Activity Recognition from User-Annotated Acceleration Data", Pervasive Computing, 2004, pp. 1-17.
Ortiz et al., "A Dynamic Sliding Window Approach for Activity Recognition", User Modeling, Adaption and Personalization, 19th International Conference, UMAP 2011, Girona, Spain, Jul. 11-15, 2011. Proceedings, pp. 1-12.
Ho, J., "Interruptions: Using Activity Transitions to Trigger Proactive Messages", Masters Thesis, Massachusetts Institute of Technology, Aug. 17, 2004, 116 pages.
Kotsiantis, S. B., "Supervised Machine Learning: A Review of Classification Techniques", Informatica, Jul. 16, 2007, 31: pp. 249-268.
Meng et al., "Displacement Estimation in Micro-sensor Motion Capture", IEEE International Conference on Systems Man and Cybernetics, Oct. 2010, pp. 2611-2618.
Sun et al., "Adaptive Sensor Data Fusion in Motion Capture", 13th Conference on in Information Fusion (Fusion), Jul. 2010, 8 pages.
International Search Report of the International Searching Authority for International Application No. PCT/US2013/032595 dated May 31, 2013.
Written Opinion of the International Searching Authority for International Application No. PCT/US2013/032595 dated May 31, 2013.
International Preliminary Report on Patentability for International Application No. PCT/US2013/032595 dated Oct. 7, 2014.

* cited by examiner

MUSCULOSKELETAL ACTIVITY RECOGNITION SYSTEM AND METHOD

RELATED APPLICATION

This application is a U.S. National Stage Entry of International Patent Application Serial No. PCT/2013/032595, titled MUSCULOSKELETAL ACTIVITY RECOGNITION SYSTEM AND METHOD, filed on Mar. 15, 2013, which claims the benefit under 35 U.S.C § 119(e) of U.S. Provisional Patent Application Ser. No. 61/686,319 filed Apr. 3, 2012, the entire disclosures of which are hereby incorporated by reference herein.

TECHNICAL FIELD

The present disclosure is related generally to skeletal and skeletal muscle monitoring. In particular, the present disclosure is directed to an apparatus and method for monitoring skeletal muscle activity and body motion using mechanomyography (MMG). More particularly, one embodiment serves the purpose of determining muscle activity, fatigue, and proper form at any time for example during regular human exercises.

BACKGROUND

Activity in both humans and even animals depends largely on functioning, active muscles. As a consequence, sensing and monitoring of muscle activity is important for many reasons. For instance, in sports medicine, information about the fatigue level of a muscle is useful for preventing over-exertion of muscles, which might lead to muscle-based injuries. In addition, sensing muscle activity could be leveraged for precision training, allowing athletes to monitor progress on targeted muscle groups as needed. Finally, other ubiquitous applications such as muscle-controlled prosthetics could also be enabled by muscle activity data.

There are two main methods for detecting and monitoring muscle activity. The first is electromyography (EMG), which accurately measures the electrical potential of active muscle fibers. By amplifying and processing these electrical signals, information about muscle activation and activity can be inferred. The second method is mechanomyography (MMG). Mechanomyographic methods use vibration transducers to detect skeletal muscle activity. A brief discussion of the physiology of skeletal muscle vibrations that enable mechanomyography based systems is provided herein.

FIG. 1 illustrates an example skeletal muscle 100 and in particular the quadriceps and the tendons 106a, 106b and muscle belly 102 (including muscle fibers 104) are shown. Skeletal muscles 100 generally consist of three parts: a muscle belly 102, composed of muscle fibers 104, and two tendon ends 106a, 106b. Activating skeletal muscles during physical activity causes the muscle fibers 104 to contract, resulting in mechanical vibrations due to: tremors of the human motor system, muscle fibers 104 sliding against each other and artifacts detected when a muscle belly's 102 circumference increases during muscle contractions and decreases during relaxation. These skeletal muscle vibrations are carried through to and detected at the skin level. The vibrations vary depending on the muscle fatigue status, muscle group size, and location in the body e.g., skeletal muscle proximity to bones of different mass and size.

As a method for inferring muscle activity, EMG while accurate, has the major setback that it is difficult, invasive and even painful to use. It requires perfect contact with the skin, necessitating the use of gels in the case of surface EMG, or the insertion of small needles into the muscle, in the case of fine-wire EMG. Mechanomyography methods on the other hand, work by externally detecting the mechanical vibrations occurring in the muscle belly of skeletal muscles when the muscle is activated using vibration transducers. As such they are less invasive and more convenient for muscle monitoring use in a dynamic environment. Current vibration transducer technologies include fabric stretch sensors, force sensitive resistors (FSR) and a combination of any of or all of available inertial sensors including accelerometers, gyroscopes and magnetometers.

SUMMARY

In one embodiment, a network of at least two distributed inertial sensor nodes are configured to communicate with each other over a first interface. Each of the inertial sensing nodes comprises at least one sensor configured to sense muscle vibrations and monitor body motion.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

In one or more various aspects, related systems include but are not limited to circuitry and/or programming for effecting herein-referenced method aspects; the circuitry and/or programming can be virtually any combination of hardware, software, and/or firmware configured to effect the herein-referenced method aspects depending upon the design choices of the system designer. In addition to the foregoing, various other method and/or system aspects are set forth and described in the teachings such as text (e.g., claims and/or detailed description) and/or drawings of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The novel features of the embodiments described herein are set forth with particularity in the appended claims. The embodiments, however, both as to organization and methods of operation may be better understood by reference to the following description, taken in conjunction with the accompanying drawings as follows:

Figure 1:
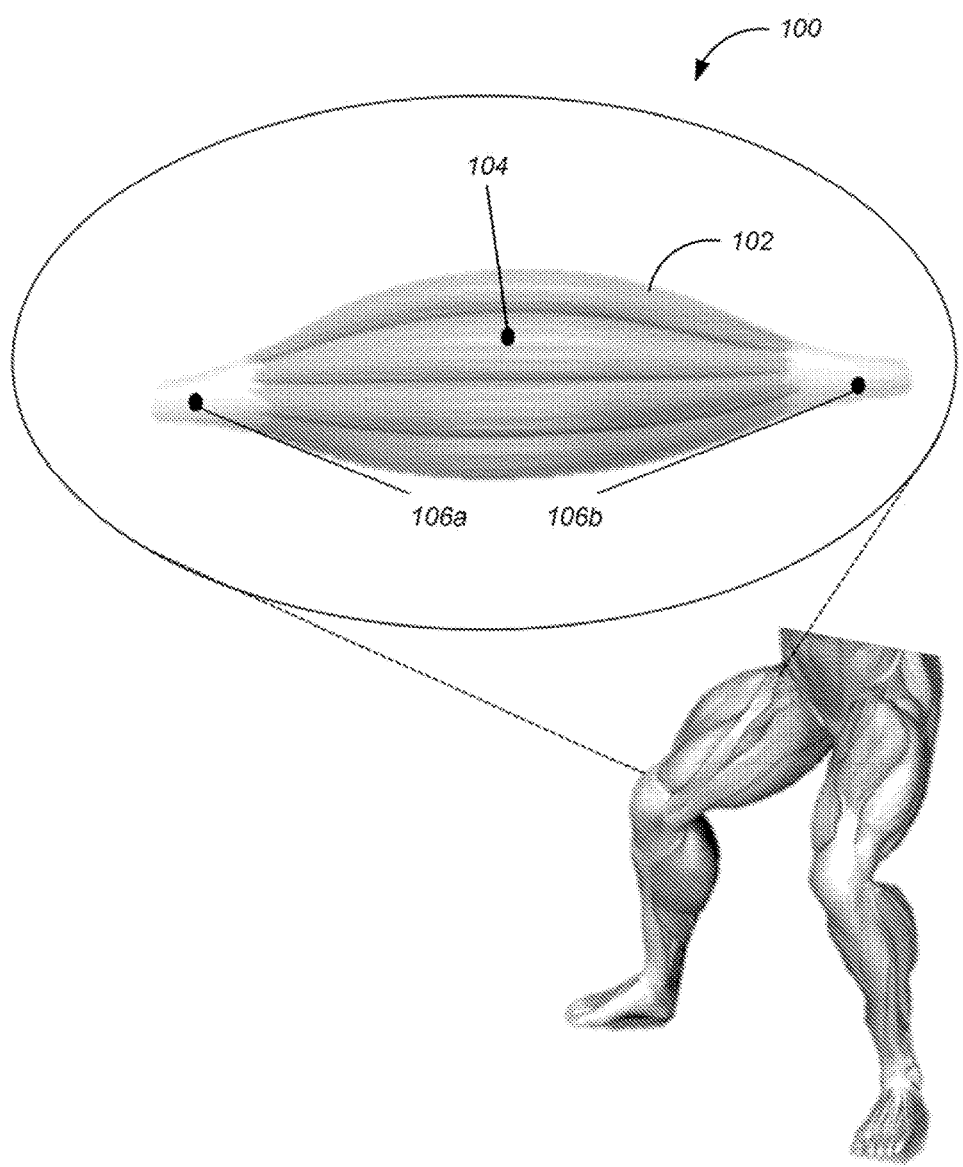
FIG. 1 is an overview of the general structure of skeletal muscle.

While the present disclosure is amenable to various modifications and alternative forms, the specifics herein have been shown by way of example in the drawings and will be described in detail. It should be understood that the intention is not to limit the present disclosure to any particular examples described. The intention is to cover all modifications, equivalents, and alternatives falling within the scope of the appended claims.

DETAILED DESCRIPTION

In the following detailed description, reference is made to the accompanying drawings, which form a part hereof. In the drawings, similar symbols and reference characters typically identify similar components throughout the several views, unless context dictates otherwise. The illustrative embodiments described in the detailed description, drawings, and claims are not meant to be limiting. Other embodiments may be utilized, and other changes may be made, without departing from the spirit or scope of the subject matter presented here.

Before explaining the various embodiments of the musculoskeletal activity recognition system and method in detail, it should be noted that the various embodiments disclosed herein are not limited in their application or use to the details of construction and arrangement of parts illustrated in the accompanying drawings and description. Rather, the disclosed embodiments may be positioned or incorporated in other embodiments, variations and modifications thereof, and may be practiced or carried out in various ways. Accordingly, embodiments of the musculoskeletal activity recognition system and method disclosed herein are illustrative in nature and are not meant to limit the scope or application thereof. Furthermore, unless otherwise indicated, the terms and expressions employed herein have been chosen for the purpose of describing the embodiments for the convenience of the reader and are not to limit the scope thereof. In addition, it should be understood that any one or more of the disclosed embodiments, expressions of embodiments, and/or examples thereof, can be combined with any one or more of the other disclosed embodiments, expressions of embodiments, and/or examples thereof, without limitation.

Also, in the following description, it is to be understood that terms such as front, back, inside, outside, top, bottom and the like are words of convenience and are not to be construed as limiting terms. Terminology used herein is not meant to be limiting insofar as devices described herein, or portions thereof, may be attached or utilized in other orientations. The various embodiments will be described in more detail with reference to the drawings.

Accordingly, various embodiments of the present disclosure are directed generally to a system, referred to herein as a Musculoskeletal Activity Recognition System (MARS), which enables the use of inertial sensors to uniquely distinguish and identify muscle activity and body motion. As used herein throughout this disclosure, the term 'subject' or 'user' will refer generally to persons using or on whom the MARS system is being used, for musculoskeletal monitoring. The MARS system and method enable sensing of skeletal muscle vibrations and body motion. The various embodiments can be more readily understood by reference to FIGS. 1-9 and the following description. While the present disclosure is not readily limited to this particular application, the present disclosure will be better appreciated by a discussion of example embodiments.

In one embodiment, a musculoskeletal sensing system is provided to sense and detect at least muscle activity, body motion or both. The sensed muscle activity data are used to distinguish the different groups of active muscle on the human body as well as understand their level of fatigue and exhaustion. The body motion data are used to track the instrumented body parts in space so that overall form and body motion can be analyzed. To enable both these sensing goals the system must consist of a highly sensitive set of distributed sensors since many multiple skeletal muscle groups and/or body parts might require instrumentation. Secondly, the system may be capable of processing the sensed data so as to be able to infer information about muscles and body motion. Such information may include but is not limited to muscle group identity, muscle fatigue as well as the orientation of body parts in space and time.

In one embodiment, the MARS system focuses on how muscle activity can be detected through processing the data collected by the inertial sensors placed topically on the human body muscles. The inertial sensors detect the muscle vibrations produced by active skeletal muscles. The sensed data are then processed to identify muscle groups and their exhaustion/fatigue status. In addition to sensing muscle activity, the MARS system also uses the inertial sensors to perform motion capture/tracking wherein the body parts instrumented with MARS system inertial sensor nodes can be accurately tracked in space and time.

Figure 2:
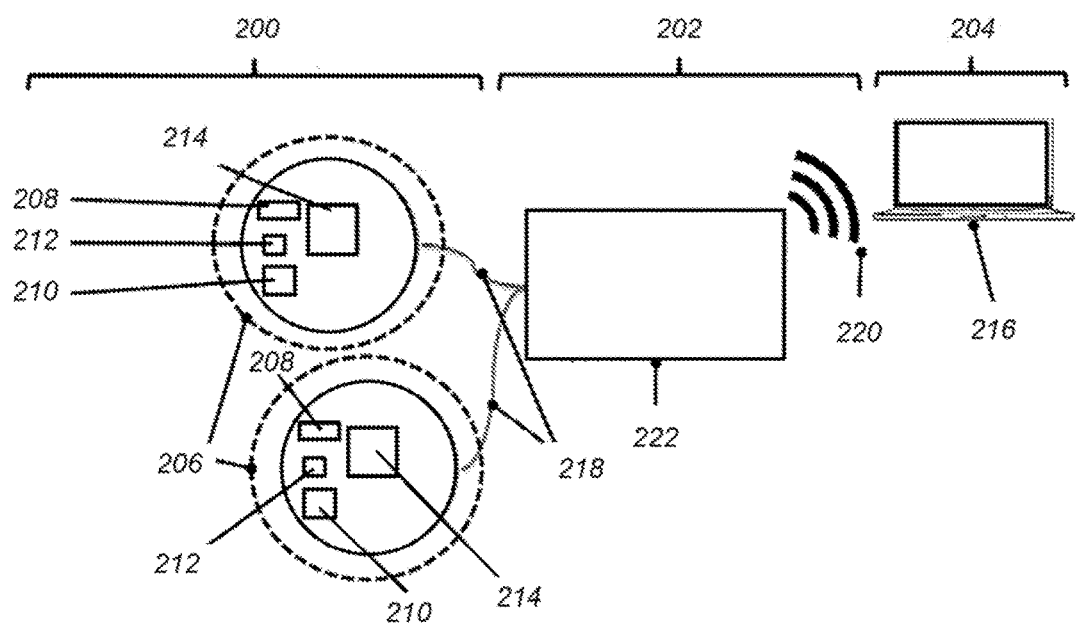
FIG. 2 is an overview of hardware components that make up one embodiment of the MARS system.
Figure 4:
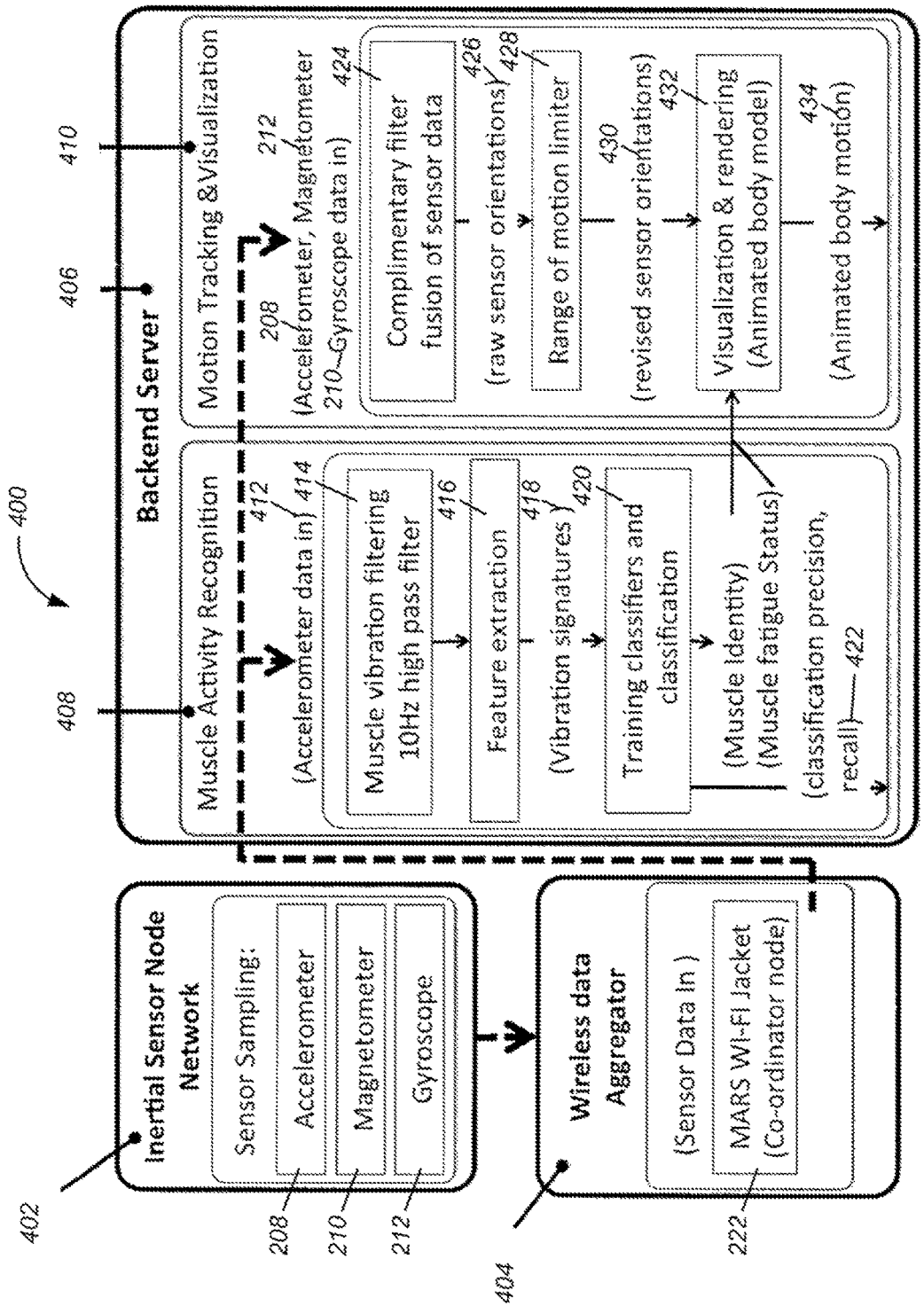
FIG. 4 is a schematic block diagram of an operational path that can be taken by a MARS system device in accordance with one embodiment.

Referring now to FIGS. 2 and 4, the MARS system, in accordance with one embodiment, may include at least three components, namely, an inertial sensor node network 200, a wireless data aggregator 202, and a backend server 204. Whereas in this embodiment there are three components, all of which are implemented in separate components, these components could be implemented using any number of components and on any number of devices. The embodiment provided here is intended to be an example implementation of the system. In other embodiments, a MARS system may comprise the inertial sensor node network 200 and a data aggregator configured to also function as a server. Still in other embodiments, a MARS system may comprise the inertial sensor node network 200 and a server configured to function as a data aggregator. Communication between any of the inertial sensor node network 200, the wireless data aggregator 202, and/or the backend server 204 may be wireless, wired, or any combination thereof. Accordingly, the various embodiments described throughout the present disclosure are limited in this context.

In the current embodiment, the inertial sensor node network 200 is made up of a group of inertial sensor nodes 206.

In one embodiment, the inertial sensor node network 200 comprises at least two distributed inertial sensing units capable of inter-sensor interaction, where each unit comprises at least one accelerometer, one gyroscope and one magnetometer capable of sensing muscle vibrations and monitoring body motion. The at least two distributed inertial sensing units may be highly sensitive. More specifically, the networked sensor units can leverage their networking to improve muscle vibration and human motion sensing ability and accuracy.

In accordance with embodiment disclosed in FIG. 2, each inertial sensor node 206, in accordance with the current example, comprises at least one of a microelectromechanical systems (MEMS) triple axis accelerometer 208 device, a MEMS triple axis gyroscope 210 device, a solid-state Hall effect triple axis magnetometer 212 device and a microcontroller 214 chip, wherein the microcontroller 214 chip comprises at least a processor and a memory coupled to the processor. The wireless data aggregator 202 is a data communication device capable of wireless transmission and as per the given example is made up of a wireless data aggregator 202 such as the MARS system Wi-Fi jacket 222. The data aggregator 202 also may be implemented using a wired connection. The backend server 204, as per the given example, comprises a computing/processing device such as a computer 216. According to the current embodiment, the sensor nodes 206 in the inertial sensor node network 200 and the wireless data aggregator 202 are inter-connected via a wired connection 218. The wireless data aggregator 202 is, in the current example, linked to a device 216, via a direct wireless Wi-Fi link 220. This link 220 may be implemented in any number of ways including direct wired, direct wireless, a combination of direct wired and direct wireless or even through the Internet or a routing device such as a router. Each of these three components, according to the current embodiment, is described in further details below.

Inertial Sensor Node Network

Referring to FIGS. 2 and 4, in one embodiment, the inertial sensor node network 200 component of MARS system comprises a plurality of inertial sensor nodes 206 that enable fine-grained, e.g., high resolution, activity sensing by detecting body motion as well as the skeletal muscle vibrations. In one embodiment, the inertial sensor node network 200 component of MARS system comprises of up to 14 small unobtrusive inertial sensor nodes 206 that enable fine-grained activity sensing by detecting body motion as well as the skeletal muscle vibrations. In other embodiments, more than 14 inertial sensor nodes may be employed, without limitation. In the current example, the role played by each sensor node 206 in the sensor node network 200 is shown by reference number 400 in FIG. 4.

Figure 3:
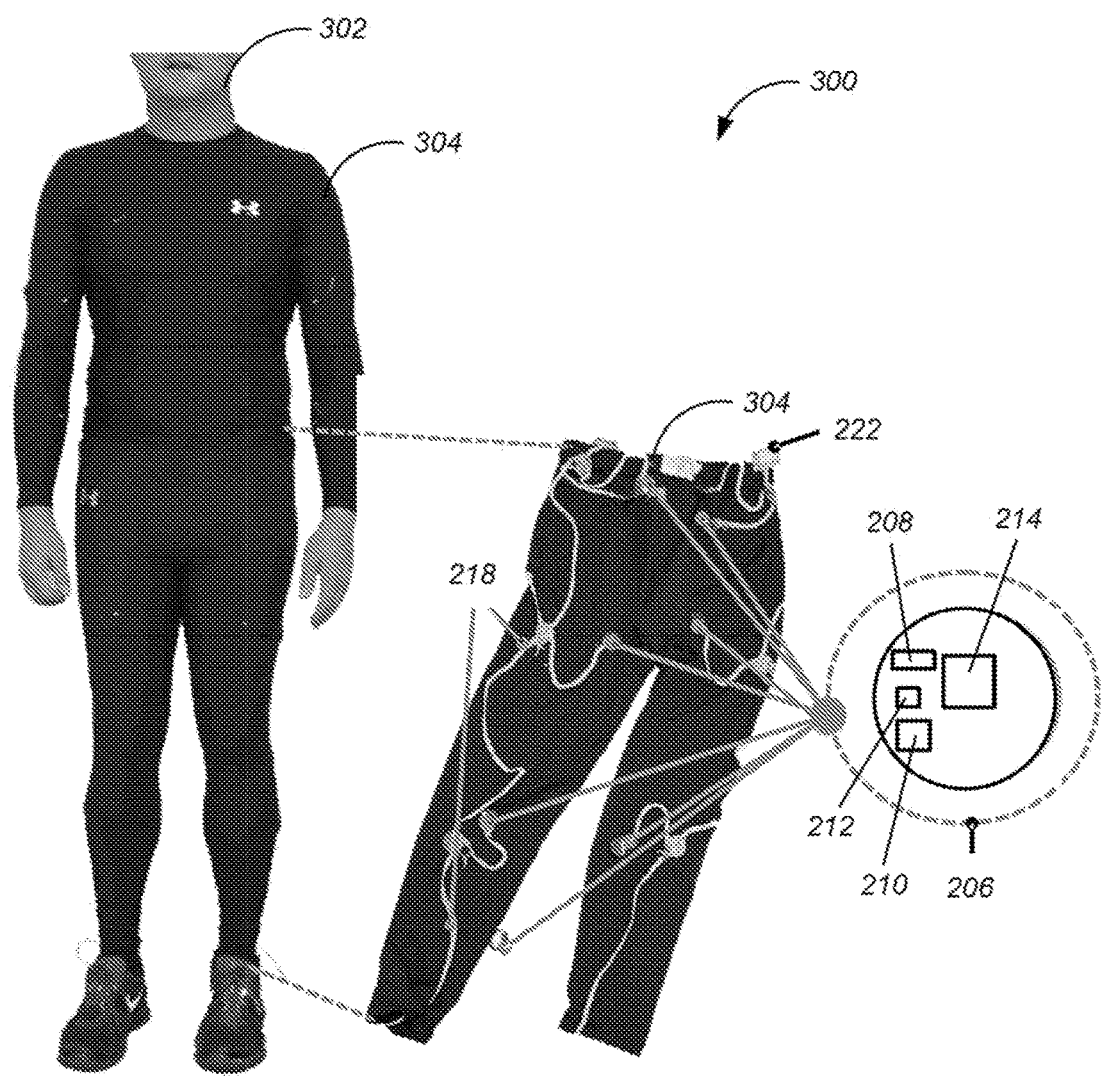
FIG. 3 is an illustration of a possible wearable physical implementation of one embodiment of a MARS system in which the hardware components shown in FIG. 2 are sewn into garments.

FIG. 3 is an illustration of a possible wearable 300 physical implementation of one embodiment of a MARS system in which the hardware components shown in FIG. 2, such as the inertial sensor nodes 206, are sewn into garments 304 that can be worn by a subject 302. The placement of the sensor nodes 206 in one wearable 300 embodiment of the MARS system is shown in FIG. 3.

With reference now to FIGS. 1-3, in one embodiment, each inertial sensor node 206 in the inertial sensor node network 200 comprises at least one of three inertial sensors: a triple axis accelerometer 208, a triple axis gyroscope 210, and a triple axis magnetometer 212. Each inertial sensor node 206 also contains an on-board microcontroller 214 that controls the sampling of the sensor nodes 206. To sense the skeletal muscle vibrations, the current example uses only data from the triple axis accelerometer 208 of the inertial sensor nodes 206 to perform muscle identity inference. However, in accordance with the current embodiment, data from the accelerometer 208, gyroscope 210 and magnetometer 212 are all fused and used for body motion tracking. To ensure the integrity of the sensed data, each inertial sensor node 206 in the current example, encodes an extra longitudinal parity checksum word to its inertial data stream. It will be appreciated that an inertial sensor node network 200 may comprise a plurality of inertial sensor nodes 206 where each inertial sensor node 206 comprises a subset of inertial sensors, e.g., accelerometer, gyroscope, magnetometer, among others, or may comprise additional inertial sensors.

In the current embodiment of the MARS system, each inertial sensor node 206 in the inertial sensor node network 200 is consolidated into a circular inertial measurement unit, implemented as follows. In the current embodiment, the node's microcontroller 214 is implemented with an ATmega128RFA1 chip available from Atmel Corporation. The accelerometer 208 is implemented using an ADXL345 Digital Accelerometer board available form Analog Devices. The gyroscope 210 is implemented using an ITG3200 board available from InvenSense Inc. The magnetometer 212 is implemented using an HMC58833L 3-Axis Digital Compass IC available form Honeywell International Inc. It will be appreciated that these components of the inertial sensor node 206 may be replaced with equivalent components without limiting the scope of the present disclosure. In the current example, the microcontroller 214 is linked to the accelerometer 208, gyroscope 210, and magnetometer 212 via an internal wired I$^2$C bus interface. In the current embodiment, to form the inertial sensor node network 200, the sensor nodes 206 are connected to each other and to the mobile wireless data aggregator 202 using a wired Serial Peripheral Interface (SPI) 218 bus running at a frequency of about 2 Mbps, for example. Each sensor node 206 in the current example can be sampled at a nominal rate of about 200 Hz, for example.

In one example of the MARS system, the inertial sensor nodes 206 interconnecting wires are either attached to the subject 302 using elastic bands or sewn into snugly fitting athletic clothing as shown in FIG. 3. In one example, the inertial sensor nodes 206 are placed so that they are located at the estimated center of the muscle belly of a major skeletal muscle.

Wireless Data Aggregator

Referring to FIGS. 1 and 2, the wireless data aggregator 202 component of the MARS system, in the current example, is responsible for performing the low-level, time-critical scheduling/coordinating of the data sampling on each of the inertial sensor nodes 206 in the network 200 as well as ensuring user mobility by enabling wireless transmission of sensor data the to the backend server computing device 216. The current embodiment of the wireless data aggregator 202 is implemented using a MARS system Wi-Fi jacket 222 wireless data aggregator device. As mentioned earlier, the data aggregator 202 also may be implemented using a wired, connection or any combination of wired and wireless methods including routing devices as well as through the Internet.

In the current embodiment, the wireless data aggregator device 222 comprises an Atmel ATmega 328P microcontroller and a MRF24WB0MA IEEE 802.11 transceiver module connected with a SPI bus running at a speed of 2 MHz, for example.

In one embodiment, the wireless data aggregator device 222 achieves the time-critical scheduling through a time division multiple access (TDMA) protocol. Using this protocol, the wireless data aggregator device 222 allocates each inertial sensor node 206 a time slot in a fixed transmission cycle in which the given node may transmit its data to the wireless data aggregator device 222. In the current embodiment, each sensor node 206 in the network 200 transmits in rapid succession, one after the other, in their allotted time slot. The wireless data aggregator device 222 periodically gathers the sampled sensor data and wirelessly transmits them to the backend server computing device 216 for processing as is shown by the flow diagram in FIG. 4 where the wireless data aggregator device 222 is represented by the enclosure labeled 404. Since the data transmitted from each sensor node 206 in the network 200 contains a checksum, the wireless data aggregator device 222 ensures that only error free data is transmitted to the computing device 216. In the current embodiment, this is achieved by decoding the checksum word in the sensor node data stream after which data packets with erroneous checksums are dropped. This preserves the integrity of the data in the MARS system. Whereas in this embodiment, the wireless data aggregator 202 is implemented in a separate device, the wireless data aggregator 202 could be implemented in more than one device or on the inertial sensor nodes 206 themselves. The embodiment provided here is intended as an example implementation of the system and not limit the scope of the invention.

Backend Server

Still with reference to FIGS. 1 and 2, the backend server 204 component of the MARS system, in the current embodiment, processes the sensor data obtained from the inertial sensor node network 200 to infer skeletal muscle activity as well track body motion in real time. In the current example, the backend server 204 comprises a backend server computing device 216 as shown in FIG. 2.

In the current example, to infer skeletal muscle activity for identifying muscles and determining muscles' level of fatigue, as well as to capture body motion, the backend server 204 computing device 216 relies on two software modules 406 as shown in FIG. 4. Additional or fewer software modules may be employed, without limitation. The first software module is a muscle activity recognition module 408. The second software module is a motion tracking and visualization module 410. We now describe in detail, the functioning of these two modules:

Muscle Activity Recognition Module 408: In the current embodiment, the first muscle activity recognition module 408 is responsible for performing muscle identity inference using 'vibration signatures'. Vibration signatures are digital representation of an instrumented muscle group in the MARS system. In the current embodiment, the vibration signatures comprise a set of feature vectors extracted only from the data stream obtained from the accelerometer 208 component of the sensor node network 200. We now describe how the vibration signatures are obtained, in one example, in accordance with the first software module 408 shown in FIG. 4.

The first step in creating muscle vibration signatures is collection of muscle vibration data 412, when muscles are being worked such as during an exercise or activity. In one example, the exercises shown in FIG. 7A-D were used to collect muscle vibration signatures from the major muscles of the human leg namely: the quadriceps, hamstrings and calves from healthy human subjects. The exercises were determined and supervised by a certified personal trainer and physiotherapist.

Exercises shown in FIGS. 7A-C are isolation exercises, meaning that they largely work a single muscle group. The Leg extension, exercise A, works the quadriceps (Q). The Leg curl, exercise B, works the hamstrings (H), and the Calf raise, exercise C, works the calves (C). Since isolation muscles largely work a single muscle, data collected during these exercises was, in the current example, used for muscle fatigue analysis, since fatigue encountered during the exercise could be largely attributed to the worked muscle.

The exercise shown in FIG. 7D, the squat, is a compound exercise, which works the Q, H, C and gluteus (G) muscles. Since the squat works all the muscles of the human leg, data collected during the squat was, in the current example for distinguishing muscles from each other.

Once collected, the vibration data is filtered. This is achieved by passing the accelerometer data stream through a digital 10 Hz high pass filter 414, as shown in FIG. 4. High pass filtering 414 is an effective technique to isolate the high frequency component (>10 Hz<100 Hz) of the data received form the accelerometer 208 from the lower frequency components (0 Hz<10 Hz). By doing this, the sensor data resulting from muscle vibration (high frequency component) can be considered without the influence sensor data due to gravity, the body motion or tremors (low frequency component).

Figure 5A:
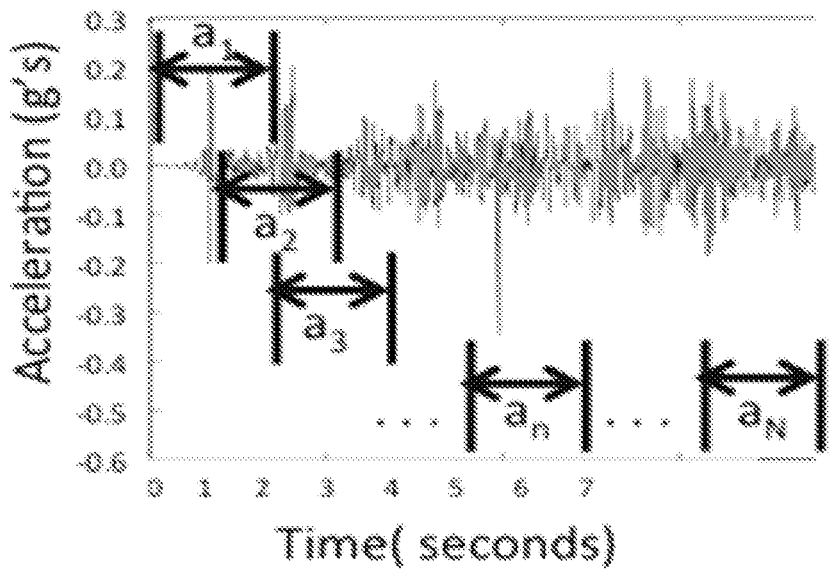
FIGS. 5A and 5B are visual representations of an example implementation of a feature extraction process as employed by one embodiment of the MARS system in the time domain (top FIG. 5A) and frequency domain (bottom FIG. 5B).
Figure 5B:
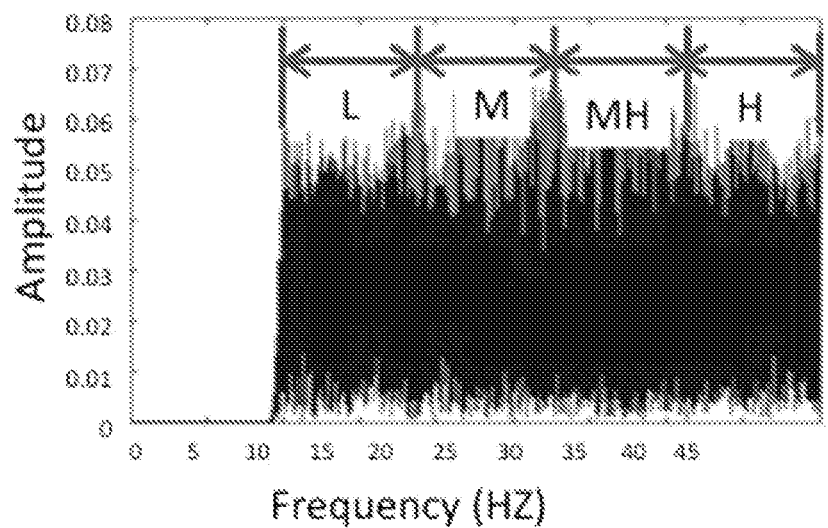

The second step in creating the muscle vibration signatures is feature extraction 416, as shown in FIG. 4. Once the accelerometer data stream has been filtered 414, the features that make up the muscle vibration signatures 418 need to be created. In the current example, to obtain these features, the muscle activity recognition module 408 calculates a selected set of 21 feature vectors, $x_m$, where m is in the range [1, 2, . . . , 21]. Of these, six are time domain features, and 15 are frequency domain features. The visual representation of one example of this process is shown in FIGS. 5A, 5B. It will be appreciated the fewer or additional features may be obtained without departing from the scope of the present disclosure.

The exemplary time domain features are signal root mean square and cosine correlation (between the accelerometer axes). The root mean square is used as a feature because it relates to the intensity with which an action is performed, in the present case, the intensity of the muscle vibration. The cosine correlation is useful in capturing the relationship between the muscle vibrations occurring along different accelerometer axes.

As is shown FIG. 5A (top "Example Accelerometer Signal"), in one example, each time domain feature vector instance is calculated using a fixed sliding window approach with 50% overlap, on the filtered time series accelerometer data stream. Each window consists of 'a' sensor data readings or points, where 'a' is 256 in the current embodiment. In one example, the windows are considered in a consecutive fashion, starting with window '$a_1$' down to window '$a_N$', for a total of N windows. A 50% overlap method is used so as to allow for smooth transitions from one feature instance to the next. This is important to capture the dynamics relating the vibrations occurring during the two phases of human muscle activity, the contraction and relaxation phases. This approach yields a total of six time domain feature vectors, $x_m$, $m \in [1, 2, 3, . . . , 6]$ of same length, N.

The number N here is also the number of windows used and depends on the size of the incoming accelerometer data stream used for creating the muscle signatures.

The selected frequency domain features include a measure of signal frequency domain entropy and signal power spectral density. The signal power spectral density measurement is useful for distinguishing muscle vibrations whose amplitude is spread out over a range of frequencies from those whose amplitude is more sharply focused at a specific frequency band. For distinguishing smoother and more uniform vibrations from discordant and jerky vibrations, which may have similar power spectral densities, the signal frequency domain entropy is used.

To obtain the frequency domain feature vectors, the muscle activity recognition module 408 takes the filtered accelerometer time series data contained in each respective window '$a_n$' and calculates a Discrete Fourier Transform (DFT). The windows, '$a_n$', are the same used in the calculation of the time domain features. The module calculates a single instance of the signal entropy per accelerometer 208 axis for each sliding window. The signal frequency domain entropy is calculated as the normalized information entropy of the DFT component magnitudes of the signal per window. This yields three, $x_m$, $m \in [7, 8, 9]$), of the 15 frequency domain features, one for each axis of the accelerometer data.

Referring to FIG. 5B (bottom "Example Signal Spectrum Over Sample Window $a_n$"), the signal power per window is also calculated over each axis as well as each sliding window, '$a_n$'. However, four feature instances are produced per sliding window per axis, instead of a single feature instance as shown in FIG. 5 (bottom). The frequencies obtained from the DFT of the time series data of each window, '$a_n$', is divided into four contiguous parts or frequency range bands i.e., (low (L), medium (M), medium high (MH) and high (H)). The signal power spectrum measurement calculated over each part. The power spectrum of the signal is estimated as the squared magnitude of the DFT amplitudes of each portion of the sliding window. This process yields four feature vectors per axis of the accelerometer, for a total of 12 more $x_m$, $m \in [10, 11, 12, \ldots, 21]$, feature vectors of equal length N.

In one embodiment, the signal power spectrum measurement may be calculated this way to allow the MARS system to determine a shift in vibration data frequency between sliding windows. Two sliding windows that may have the similar frequency domain entropies at different frequency bands can be distinguished.

The six time domain and 15 frequency domain feature vectors are combined into a single matrix X, shown below of dimension N by M, M=21 on a per muscle basis. This matrix X is the digital representation of the vibration signal that is obtained from the inertial sensor node 206 placed on each instrumented muscle group. It is this matrix of feature vectors that constitutes the unique vibration signature of the particular muscle group. The matrix form of the muscle vibration signature as is stored by the MARS system is shown below.

$$\text{Vibration Signature} \rightarrow X_{n,m} = \begin{pmatrix} x_{1,1} & x_{1,2} & \ldots & x_{1,M} \\ x_{2,1} & x_{2,2} & \ldots & x_{2,M} \\ \vdots & \vdots & \ddots & x \\ x_{N,1} & x_{N,2} & \ldots & x_{N,M} \end{pmatrix}$$

With the creation of the vibration signatures, the mechanical vibrations are transformed into a digital representation that can be used to build a muscle identity classifier.

The next step is to train a classifier 420 on the calculated features which will be used to classify/infer skeletal muscle identities as well as the state of skeletal muscle fatigue. In the current embodiment of the MARS system, this may be achieved using supervised machine learning techniques, for example.

By supervised machine learning, we mean that in order for the MARS system to match new future feature instances to a particular muscle group, it must first be trained using a labeled initial set of muscle vibration signatures 418 obtained over a specific training period from the given muscle group. Therefore, the MARS system activity recognition module is initially provided with both the muscle vibration signatures 418 and an accompanying set of labels, stating the muscle group that the signatures 418 belong to. This initial set of muscle vibration signatures 418 and labels constitutes the training data used to train a supervised classifier 420.

Once training data is obtained, the muscle activity recognition module 408, in the current embodiment, builds a J48 decision tree (DT) supervised classifier. This classifier is implemented using WEKA (Waikato Environment for Knowledge Analysis) software, a popular suite of machine learning software written in Java, developed at the University of Waikato, New Zealand. This classifier will be used to assign labels or muscle identities to future new incoming vibration feature data points. In general the DT algorithm learns a hypothesis $h \in H$, (where $H=\{h:h|X \rightarrow Y\}$ is the space of all functions that can approximate the target function $f: X \rightarrow Y$), to match vibration signatures 418 to muscle groups. X in this case is the N by M vibration signature matrix corresponding to each muscle group, comprised of the set of 21 feature vectors $X = \langle x_1, x_2, \ldots, x_m \rangle$, (M=21). Y is the vector of K classes intended for prediction, $\{y^{muscle\ grp1}, y^{muscle\ grp2}, \ldots, y^{muscle\ group\ k}\}$. In the current example system K=8 and muscle grp1=quadriceps, muscle gpr2=hamstrings, muscle grp3=calves, muscle grp4=gluteus muscle gpr5=biceps, muscle grp6=triceps, muscle gpr7=trapezius and muscle grp8=pectorals.

In the current implementation, the function/hypothesis (classifier) h that the MARS system learns for each muscle group will predict a class $\{y^{muscle\ grp1}, y^{muscle\ grp2}, \ldots, y^{muscle\ group\ k}\}$ for a new $j^{th}$ incoming set of feature instances $\langle x_1^j, \ldots, x_M^j \rangle$ calculated from specific sensor data. The learned classifiers are stored locally on the backend server 204 in form of classifier objects for future reference. In one example a 10-fold cross validation is performed when identifying each leg muscle using one example of the classifier objects, on data obtained from 10 subjects instrumented with the MARS system performing the exercises shown in FIGS. 7A-D. The precision and accuracy results of this classification task for the compound squat exercise are reported in FIG. 8, which is a graph 800 of the accuracy in terms of precision and recall 422, of distinguishing the muscle groups of a human leg, during a leg extension, according to one embodiment. In another example, a 10-fold cross validation is performed when identifying the fatigue level of the quadriceps muscle using another classifier object, on data obtained from the same subjects instrumented with the MARS system during a leg extension exercise. The precision and accuracy results of this classification task are reported in FIG. 9, which is a graph 900 of the accuracy in terms of precision and recall 422 of distinguishing the state of an example muscle, in this given case, the quadriceps, as either fresh or fatigued, during a leg extension, according to one embodiment. These results show that the MARS system can leverage detected muscle vibrations to distinguish leg muscles (quadriceps, hamstrings and calves) and determine muscle fatigue status with greater than 90% precision and recall.

With reference now back to FIG. 4, after the classifier training step 420, the system becomes self-tagging. The MARS system sensor nodes 206 can be shifted around, removed and even damaged sensor nodes 206 replaced without crippling the system. Once powered up again, new sensor readings are taken, and the data is classified using the stored classifier objects. The classifier that best fits the data is used to infer the identity of the muscle, which the sensors are instrumenting.

The current embodiment of the accelerometer data processing including the features, feature extraction process, classification technique and overall structure of the Muscle Activity Recognition Module 408 provided here is intended as an example and should not be considered as limiting the scope of the invention. The muscles monitored in this embodiment are human but in the scope of the present disclosure, the technique described here in may be used to monitor skeletal muscle on other animals as well.

Motion Tracking and Visualization Module 410: In the current embodiment, the motion tracking and visualization module 410 is responsible for fusing sensor data to obtain sensor/body part orientations as well as visualizing the orientations using an animated avatar/human body model. We describe here how in one example, motion tracking is realized, as shown in FIG. 4.

The first step undertaken by the motion tracking and visualization module 410 is the complimentary filter fusion of inertial sensor nodes 206 data. This step is useful since inertial sensors, namely the accelerometer 208, gyroscope 210 and magnetometer 212 exhibit readings with drift especially as the sensors 208, 210, 212 are moved. As a result, to obtain accurate orientations of the sensors 208, 210, 212, fusion of sensor data is necessary. This helps mitigate the shortcomings of either sensor with a counterpart sensor.

The motion tracking module achieves this goal through a quaternion-based complimentary filter 424. The complimentary filter 424 effectively works as a high-pass filter for the gyroscope 210 data stream and a low-pass filter for the data streams received from the accelerometer 208 and magnetometer 212.

This enables the motion tracking and visualization module 410 of the MARS system to leverage the accelerometer 208 and magnetometer 212 data streams to provide the absolute orientation over time where they provide reliable absolute orientation information. Integrated over time, the accelerometer 208 axis aligned with gravity and the magnetometer 212 axis aligned with magnetic north or the dominant local magnetic field will, have dominant readings respectively. These readings are used to reduce gyroscope 210 data drift by providing a known reference location from which rotational angles can be measured.

Over short or instantaneous periods of time, the gyroscope 210 data stream provides accurate degrees per second (°/s) measurements on rotational sensor orientation changes. Consequently, for instantaneous orientation information, the complimentary filter relies on the gyroscope 210 data to correct for the results obtained from the accelerometer 208 and the magnetometer 212 data streams.

Once sensor orientations 426 on the body have been found, the motion tracking and visualization module 410 associates them with the body part to which the sensors are attached to yield individual raw body part orientations. The sensor to body location mapping is obtained from the muscle inference information from the muscle activity recognition module 408 previously described. Since specific muscle groups are located on specific body parts, the motion recognition and visualization module 410 can infer the sensor location on the body.

Once obtained, the estimated raw sensor orientations 426 of the body parts attached to certain sensors need to be refined because they may defy the limits of the normal human body, due to inertial sensor data drift. To correct for this, the raw sensor orientations are passed through a range of motion limiter 428. The range of motion limiter 428 offsets the errors and restricts the orientations obtained from the complimentary filter 424 to match the capabilities of the human body. Accordingly, revised sensor orientations 430 are produced.

Figure 6:
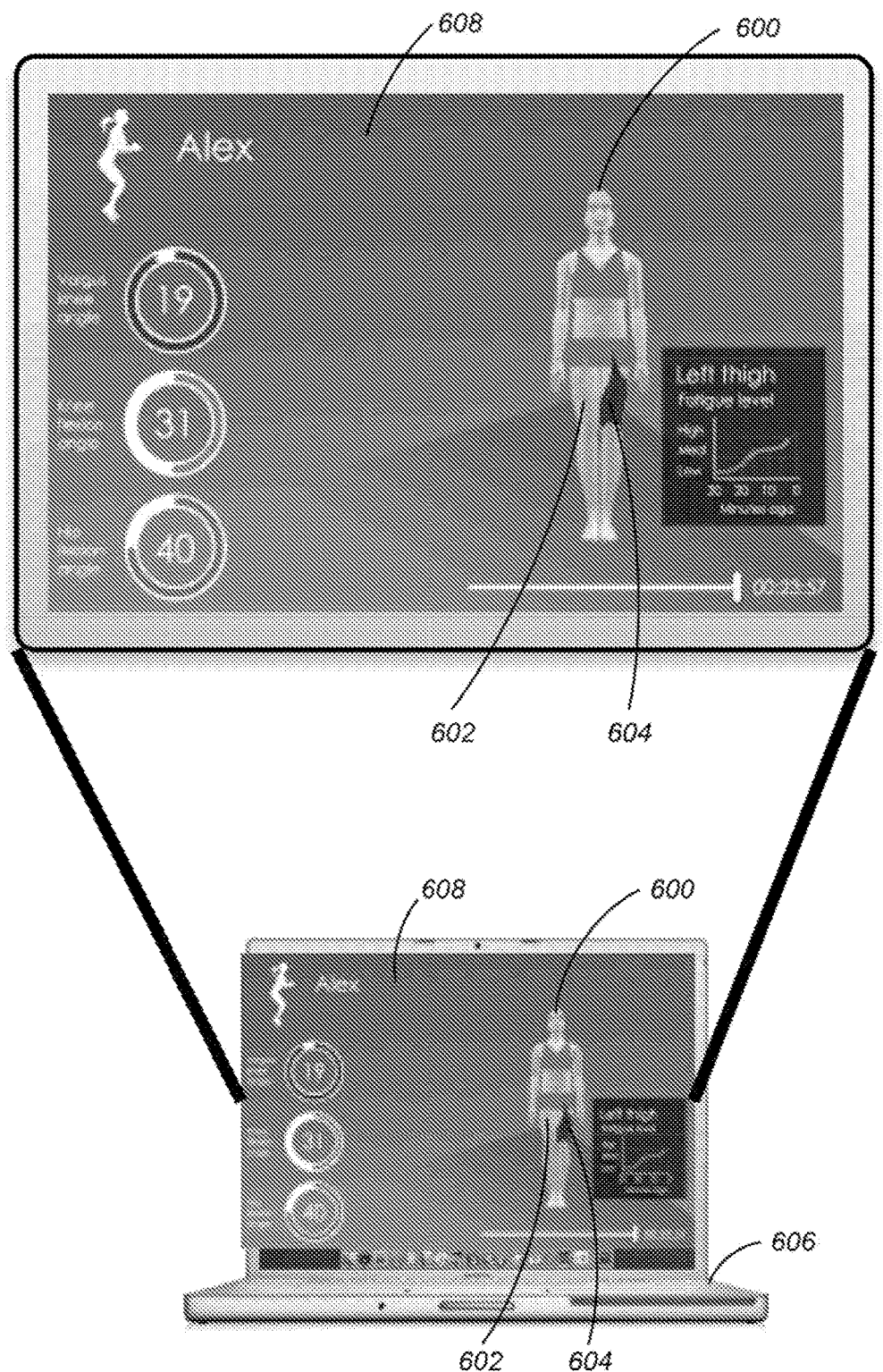
FIG. 6 is an example screen shot of a human-like avatar used for visual representation of muscle activity and body motion of persons instrumented provided by one embodiment of the MARS system.
Figure 7:
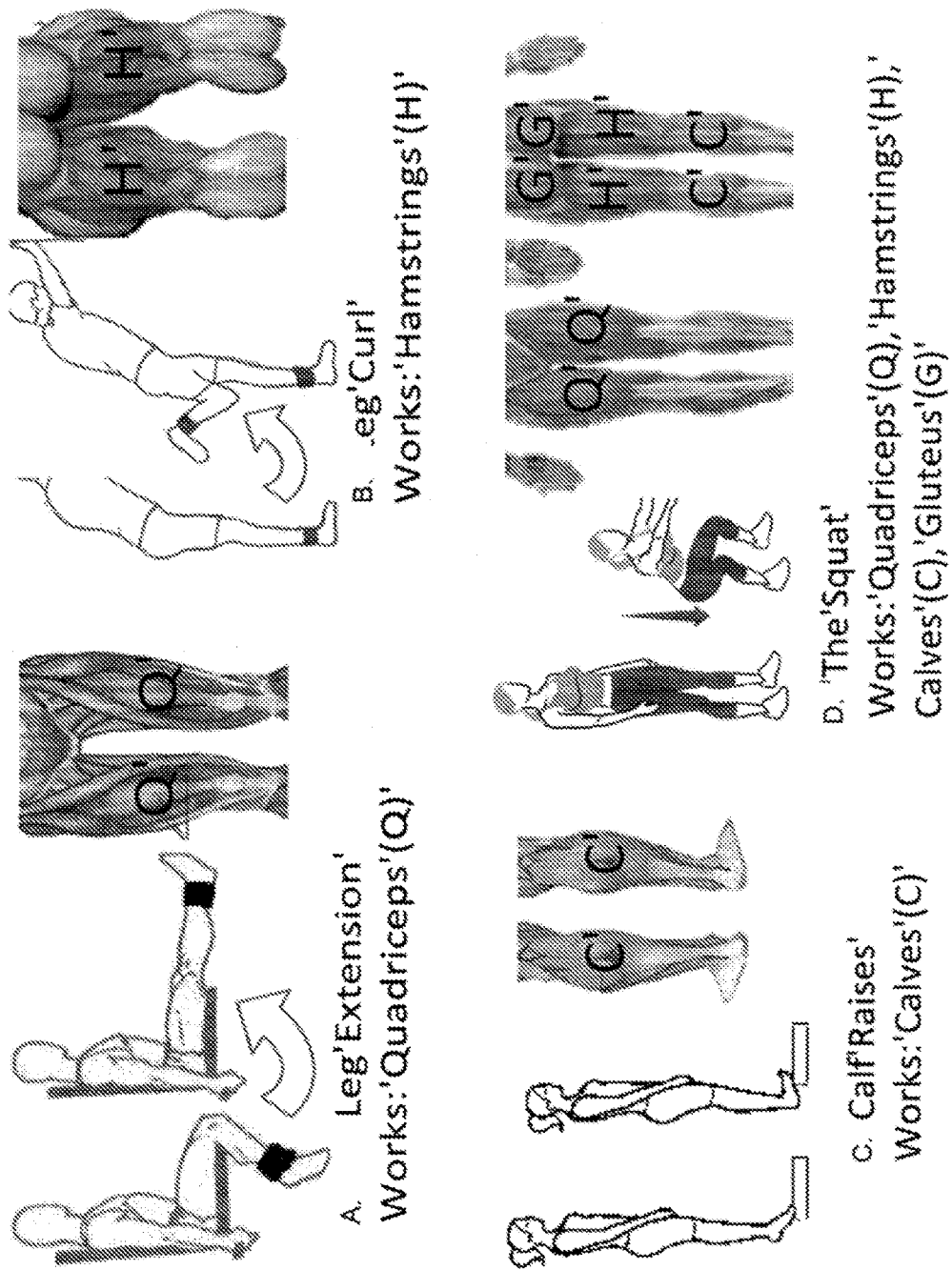
FIGS. 7A-D show an example subset of exercises used to gather data for training, testing and validating one embodiment of the MARS system.
Figure 8:
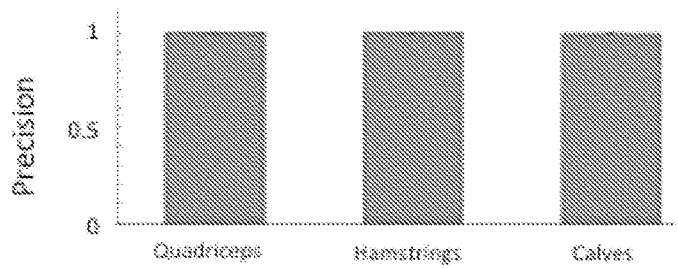
FIG. 8 is a graph of the accuracy in terms of precision and recall, of distinguishing the muscle groups of a human leg, during a leg extension, according to one embodiment.
Figure 9:
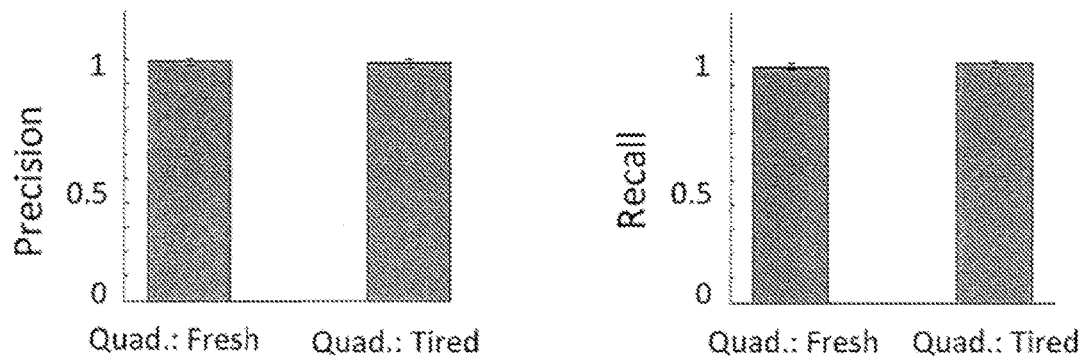
FIG. 9 is a graph of the accuracy in terms of precision and recall of distinguishing the state of an example muscle, in this given case, the quadriceps, as either fresh or fatigued, during a leg extension, according to one embodiment.

The final step performed by the motion tracking and visualization module 410 is visualization 432. Visualization 432 is necessary in order for a human to use the revised body part orientations 430 for analysis of body motion. This goal is achieved, in the current embodiment, using an animated human-like avatar 600 displayed on a display portion 608 of a computing device 606 as shown in FIG. 6. The visualized body parts 602, 604 of the avatar 600 correspond to the instrumented points on a real human subject. As the revised body part orientations 430 are received, the animated avatar 600 moves to mimic the motion of the instrumented human subject. The muscles 602, 604 of the avatar 600 are also highlighted in different colors to represent the fatigue status of the instrumented muscle.

Figure 10:
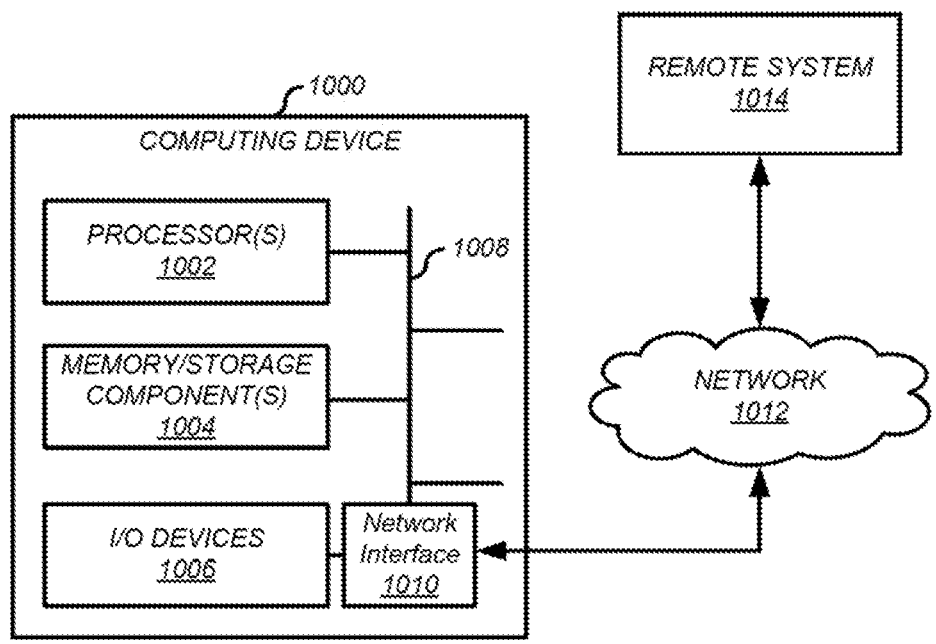
FIG. 10 illustrates a computing device to implement various aspects of a backend server node of a MARS system, according to various embodiments of the present disclosure.

FIG. 10 illustrates one embodiment of a computing device 1000 which can be used in one embodiment of a system to implement various embodiments of the backend server node 204 set forth in this disclosure. The computing device 1000 may be employed to implement one or more of the computing devices according to the disclosed embodiments or any other suitably configured computing device. The computing device 1000 may be employed to execute computer readable instructions associated with executing the operational path that can be taken by a MARS system device in accordance with the embodiment depicted by way schematic block diagram in FIG. 4. In particular, the computing device 1000 may be employed to execute computer readable instructions associated with the muscle activity recognition module 408 and the motion tracking and visualization module 410, including executing the J48 DT supervised classifier implemented using WEKA and the visualizing the orientations using an animated avatar/human body model.

For the sake of clarity, the computing device 1000 is illustrated and described here in the context of a single computing device. It is to be appreciated and understood, however, that any number of suitably configured computing devices can be used to implement any of the described embodiments. For example, in at least some implementations, multiple communicatively linked computing devices are used. One or more of these devices can be communicatively linked in any suitable way such as via one or more networks. One or more networks can include, without limitation: the Internet, one or more local area networks (LANs), one or more wide area networks (WANs) or any combination thereof.

In this example, the computing device 1000 comprises one or more processor circuits or processing units 1002, one or more memory circuits and/or storage circuit component(s) 1004 and one or more input/output (I/O) circuit devices 1006. Additionally, the computing device 1000 comprises a bus 1008 that allows the various circuit components and devices to communicate with one another. The bus 1008 represents one or more of any of several types of bus structures, including a memory bus or memory controller, a peripheral bus, an accelerated graphics port, and a processor or local bus using any of a variety of bus architectures. The bus 1008 may comprise wired and/or wireless buses.

The processing unit 1002 may be responsible for executing various software programs such as system programs, applications programs, and/or modules to provide computing and processing operations for the computing device 1000. The processing unit 1002 may be responsible for performing various voice and data communications operations for the computing device 1000 such as transmitting and receiving voice and data information over one or more wired or wireless communications channels. Although the processing unit 1002 of the computing device 1000 includes single processor architecture as shown, it may be appreciated that the computing device 1000 may use any suitable processor architecture and/or any suitable number of processors in accordance with the described embodiments. In one embodiment, the processing unit 1002 may be implemented using a single integrated processor.

The processing unit 1002 may be implemented as a host central processing unit (CPU) using any suitable processor circuit or logic device (circuit), such as a general purpose processor and/or a state machine. The processing unit 1002 also may be implemented as a chip multiprocessor (CMP), dedicated processor, embedded processor, media processor, input/output (I/O) processor, co-processor, microprocessor, controller, microcontroller, application specific integrated circuit (ASIC), field programmable gate array (FPGA), programmable logic device (PLD), digital signal processors (DSP), or other processing device in accordance with the described embodiments.

As shown, the processing unit 1002 may be coupled to the memory and/or storage component(s) 1004 through the bus 1008. The memory bus 1008 may comprise any suitable interface and/or bus architecture for allowing the processing unit 1002 to access the memory and/or storage component(s) 1004. Although the memory and/or storage component(s) 1004 may be shown as being separate from the processing unit 1002 for purposes of illustration, it is worthy to note that in various embodiments some portion or the entire memory and/or storage component(s) 1004 may be included on the same integrated circuit as the processing unit 1002. Alternatively, some portion or the entire memory and/or storage component(s) 1004 may be disposed on an integrated circuit or other medium (e.g., hard disk drive) external to the integrated circuit of the processing unit 1002. In various embodiments, the computing device 1000 may comprise an expansion slot to support a multimedia and/or memory card, for example.

The memory and/or storage component(s) 1004 represent one or more computer-readable media and in one embodiment one or more non-transitory computer-readable media. The memory and/or storage component(s) 1004 may be implemented using any computer-readable media capable of storing data such as volatile or non-volatile memory, removable or non-removable memory, erasable or non-erasable memory, writeable or re-writeable memory, and so forth. The memory and/or storage component(s) 1004 may comprise volatile media (e.g., random access memory (RAM)) and/or nonvolatile media (e.g., read only memory (ROM), Flash memory, optical disks, magnetic disks and the like). The memory and/or storage component(s) 1004 may comprise fixed media (e.g., RAM, ROM, a fixed hard drive, etc.) as well as removable media (e.g., a Flash memory drive, a removable hard drive, an optical disk, etc.). Examples of computer-readable storage media may include, without limitation, RAM, dynamic RAM (DRAM), Double-Data-Rate DRAM (DDRAM), synchronous DRAM (SDRAM), static RAM (SRAM), read-only memory (ROM), programmable ROM (PROM), erasable programmable ROM (EPROM), electrically erasable programmable ROM (EEPROM), flash memory (e.g., NOR or NAND flash memory), content addressable memory (CAM), polymer memory (e.g., ferroelectric polymer memory), phase-change memory, ovonic memory, ferroelectric memory, silicon-oxide-nitride-oxide-silicon (SONOS) memory, magnetic or optical cards, or any other type of media suitable for storing information.

The one or more I/O devices 1006 allow a user to enter commands and information to the computing device 1000, and also allow information to be presented to the user and/or other components or devices. Examples of input devices include a keyboard, a cursor control device (e.g., a mouse), a microphone, a scanner, biometric sensors and the like. Examples of output devices include a display device (e.g., a monitor or projector, speakers, a printer, a network card, etc.). The computing device 1000 may comprise an alpha-numeric keypad coupled to the processing unit 1002. The keypad may comprise, for example, a QWERTY key layout and an integrated number dial pad. The computing device 1000 may comprise a display coupled to the processing unit 1002. The display may comprise any suitable visual interface for displaying content to a user of the computing device 1000. In one embodiment, for example, the display may be implemented by a liquid crystal display (LCD) such as a touch-sensitive color (e.g., 76-bit color) thin-film transistor (TFT) LCD screen. The touch-sensitive LCD may be used with a stylus and/or a handwriting recognizer program.

The processing unit 1002 may be arranged to provide processing or computing resources to the computing device 1000. For example, the processing unit 1002 may be responsible for executing various software programs including system programs such as operating system (OS) and application programs. System programs generally may assist in the running of the computing device 1000 and may be directly responsible for controlling, integrating, and managing the individual hardware components of the computer system. The OS may be implemented, for example, as a Microsoft® Windows OS, Symbian OS™, Embedix OS, Linux OS, Binary Run-time Environment for Wireless (BREW) OS, JavaOS, Android OS, Apple OS or other suitable OS in accordance with the described embodiments. The computing device 1000 may comprise other system programs such as device drivers, programming tools, utility programs, software libraries, application programming interfaces (APIs), and so forth.

The computer 1000 also includes a wired or wireless network interface 1010 coupled to the bus 1008. The network interface 1010 provides a two-way data communication coupling to a local network 1012. For example, the network interface 1010 may be a digital subscriber line (DSL) modem, satellite dish, an integrated services digital network (ISDN) card or other data communication connection to a corresponding type of telephone line. As another example, the communication interface 1010 may be a LAN card effecting a data communication connection to a compatible LAN. Wireless communication means such as internal or external wireless modems may also be implemented.

In any such implementation, the network interface 1010 sends and receives electrical, electromagnetic or optical signals that carry digital data streams representing various types of information, such as the selection of goods to be purchased, the information for payment of the purchase, or the address for delivery of the goods. The network interface 1010 typically provides data communication through one or more networks to other data devices. For example, the network interface 1010 may effect a connection through the local network to an Internet Host Provider (ISP) or to data equipment operated by an ISP. The ISP in turn provides data communication services through the internet (or other packet-based wide area network). The local network and the internet both use electrical, electromagnetic or optical signals that carry digital data streams. The signals through the various networks and the signals on the network interface 1010, which carry the digital data to and from the computer system 1000, are exemplary forms of carrier waves transporting the information.

The computer 1000 can send messages and receive data, including program code, through the network(s) and the network interface 1010. In the Internet example, a server might transmit a requested code for an application program through the internet, the ISP, the local network (the network 1012) and the network interface 1010. In accordance with the invention, one such downloaded application provides for the identification and analysis of a prospect pool and analysis of marketing metrics. The received code may be executed by processor 1004 as it is received, and/or stored in storage device 1010, or other non-volatile non-transitory storage for later execution. In this manner, computer 1000 may obtain application code in the form of a carrier wave.

Various embodiments may be described herein in the general context of computer executable instructions, such as software, program modules, and/or engines being executed by a computer. Generally, software, program modules, and/or engines include any software element arranged to perform particular operations or implement particular abstract data types. Software, program modules, and/or engines can include routines, programs, objects, components, data structures and the like that perform particular tasks or implement particular abstract data types. An implementation of the software, program modules, and/or engines components and techniques may be stored on and/or transmitted across some form of computer-readable media. In this regard, computer-readable media can be any available medium or media useable to store information and accessible by a computing device. Some embodiments also may be practiced in distributed computing environments where operations are performed by one or more remote processing devices that are linked through a communications network. In a distributed computing environment, software, program modules, and/or engines may be located in both local and remote computer storage media including memory storage devices.

Although some embodiments may be illustrated and described as comprising functional components, software, engines, and/or modules performing various operations, it can be appreciated that such components or modules may be implemented by one or more hardware components, software components, and/or combination thereof. The functional components, software, engines, and/or modules may be implemented, for example, by logic (e.g., instructions, data, and/or code) to be executed by a logic device (e.g., processor). Such logic may be stored internally or externally to a logic device on one or more types of computer-readable storage media. In other embodiments, the functional components such as software, engines, and/or modules may be implemented by hardware elements that may include processors, microprocessors, circuits, circuit elements (e.g., transistors, resistors, capacitors, inductors, and so forth), integrated circuits, ASIC, PLD, DSP, FPGA, logic gates, registers, semiconductor device, chips, microchips, chip sets, and so forth.

Examples of software, engines, and/or modules may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

In some cases, various embodiments may be implemented as an article of manufacture. The article of manufacture may include a computer readable storage medium arranged to store logic, instructions and/or data for performing various operations of one or more embodiments. In various embodiments, for example, the article of manufacture may comprise a magnetic disk, optical disk, flash memory or firmware containing computer program instructions suitable for execution by a general purpose processor or application specific processor. The embodiments, however, are not limited in this context.

While various details have been set forth in the foregoing description, it will be appreciated that the various aspects of the musculoskeletal activity recognition system and method may be practiced without these specific details. For example, for conciseness and clarity selected aspects have been shown in block diagram form rather than in detail. Some portions of the detailed descriptions provided herein may be presented in terms of instructions that operate on data that is stored in a computer memory. Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities.

Unless specifically stated otherwise as apparent from the foregoing discussion, it is appreciated that, throughout the foregoing description, discussions using terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

It is worthy to note that any reference to "one aspect," "an aspect," "one embodiment," or "an embodiment" means that a particular feature, structure, or characteristic described in connection with the aspect is included in at least one aspect. Thus, appearances of the phrases "in one aspect," "in an aspect," "in one embodiment," or "in an embodiment" in various places throughout the specification are not necessarily all referring to the same aspect. Furthermore, the particular features, structures or characteristics may be combined in any suitable manner in one or more aspects.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits ASICs, FPGAs, DSPs, or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, non-transitory medium, transmitting computer, receiving computer, etc. located outside the territory).

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

In summary, numerous benefits have been described which result from employing the concepts described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical application to thereby enable one of ordinary skill in the art to utilize the various embodiments and with various modifications as are suited to the particular use contemplated. It is intended that the claims submitted herewith define the overall scope.

Various aspects of the subject matter described herein are set out in the following numbered clauses:

1. A muscle activity and skeletal monitoring apparatus comprising a network of at least two highly sensitive distributed inertial sensing units, capable of inter sensor interaction and each unit of which includes at least one accelerometer, one gyroscope and one magnetometer configured to sense muscle vibrations and monitor body motion.

2. More specifically, the networked sensor units can leverage their networking to improve muscle vibration and human motion sensing ability and accuracy.

3. More specifically, the accelerometers and gyroscopes in the current example are microelectromechanical system (MEMS) devices. The magnetometers used in the current examples are solid-state Hall effect devices.

4. More specifically the inertial sensing units, in the current example are labeled with reference number 206, in FIG. 2.

5. A method for muscle activity and skeletal monitoring in which a common sensor is used for skeletal motion tracking as well as sensing muscle vibration through Mechanomyography (MMG).

6. More specifically, the common sensor in the current example is an accelerometer, where in the same current embodiment the accelerometer is a MEMS based device.

7. More specifically in one example the muscle activity recognition capability provided by the accelerometer data can be improved by incorporating data from the gyroscope and magnetometer.

8. A muscle activity recognition method capable of recognizing the unique vibration signature or fingerprint of a muscle in order for a sensing unit to automatically recognize what muscle it has been placed on.

9. A method of using the unique muscle vibration signature to build a learning algorithm to classify and distinguish different instrumented muscle groups from each other.

10. More specifically, in the current example of implementation, the machine learning technique is an implementation of a J48 decision Tree.

11. A method of using the unique muscle vibration signature to build another learning algorithm to infer the level of exertion or fatigue in a given instrumented muscle group.

12. More specifically the level of fatigue in the current example may be used to infer a time to failure of the given muscle, where a time to failure is defined in the current example as the time at which after muscle exhaustion, a subject may not be able to voluntarily activate a muscle to continue performing a task requiring that exerted/fatigued muscle.

What is claimed is:

1. A muscle activity recognition method, comprising:
   detecting, via a network of more than one inertial sensor node distributed on a physically active muscle group of a user's body, muscle vibration data, wherein each inertial sensor node comprises at least one inertial sensor including an accelerometer;
   determining, via a server communicatively coupled to each inertial sensor node, a unique vibration signature to identify the muscle group of the user's body, wherein the unique vibration signature is determined from a stream of muscle vibration data compiled from each accelerometer of each inertial sensor node, and wherein the server is configured to execute a muscle activity recognition module programmed to:
      filter the stream of muscle vibration data through a high pass filter;
      extract features from the filtered stream of muscle vibration data by calculating a select set of feature vectors;
      combine the select set of feature vectors into a matrix, wherein the matrix constitutes the unique vibration signature associated with the muscle group of the user's body; and
      identify, via a classifier, the muscle group of the user's body corresponding to the determined unique vibration signature based on the calculated select set of feature vectors; and
   presenting, via a user interface, a human-like avatar comprising a plurality of visualized body parts, wherein the identified muscle group of the user's body is highlighted on its corresponding visualized body part of the human-like avatar to distinguish different physically active muscle groups of the user's body and to monitor the identified muscle group of the user's body.

2. The muscle activity recognition method of claim 1, wherein the identifying of the muscle group of the user's body is based on classifier objects stored on the server.

3. The muscle activity recognition method of claim 1, wherein calculating the select set of feature vectors comprises:
   calculating a first number of time domain feature vectors and a second number of frequency domain feature vectors.

4. The muscle activity recognition method of claim 3, wherein each time domain feature vector is calculated using a sliding window technique with either a fixed or a variable overlap on the filtered stream of muscle vibration data.

5. The muscle activity recognition method of claim 4, wherein the sliding window technique with the fixed overlap is used, and wherein each frequency domain feature vector is calculated via a discrete Fourier transform on the filtered stream of muscle vibration data contained in each fixed sliding window.

6. The muscle activity recognition method of claim 1, further comprising:
   training the classifier using a supervised machine learning technique.

7. The muscle activity recognition method of claim 1, wherein the classifier comprises a J48 decision tree classifier.

8. The muscle activity recognition method of claim 1, further comprising:
   detecting muscle vibration data for a single muscle group during an isolation exercise, wherein the muscle vibration data varies based on a fatigue status of the single muscle group;
   determining a fresh vibration signature from muscle vibration data associated with the single muscle group in a fresh state and a fatigued vibration signature from muscle vibration data associated with the single muscle group in a fatigued state; and
   training the classifier using a supervised machine learning technique using the fresh vibration signature and the fatigued vibration signature;
   wherein the server is configured to execute the muscle activity recognition module further programmed to identify, via the classifier, the muscle group of the user's body as fresh or fatigued if the identified muscle group corresponds to the single muscle group and the determined unique vibration signature corresponds to the fresh vibration signature or the fatigued vibration signature respectively; and
   wherein the method further comprises highlighting the identified muscle group of the user's body on its corresponding visualized body part of the human-like avatar in a first way if the identified muscle group of the user's body is fresh and in a second way if the identified muscle group of the user's body is fatigued to prevent over-exertion of the identified muscle group of the user's body.

9. The muscle activity recognition method of claim 1, further comprising:
   detecting, via the network of more than one inertial sensor node distributed on the physically active muscle group of the user's body, body motion data, wherein each inertial sensor node comprises a plurality of inertial sensors including the accelerometer, a gyroscope, and a magnetometer; and tracking, via the server, an orientation of the more than one inertial sensor node over time, wherein the server is configured to execute a motion tracking and visualization module programmed to:
- filter a stream of accelerometer body motion data, compiled from each accelerometer of each inertial sensor node, through a complimentary filter functioning as a low-pass filter;
- filter a stream of gyroscope body motion data, compiled from each gyroscope of each inertial sensor node, through the complimentary filter functioning as a high-pass filter;
- filter a stream of magnetometer body motion data, compiled from each magnetometer of each inertial sensor node, through the complimentary filter functioning as a low-pass filter;
- correct drift associated with the filtered stream of accelerometer body motion data based on at least one of the filtered stream of gyroscope body motion data or the filtered stream of magnetometer body motion data;
- correct drift associated with the filtered stream of gyroscope body motion data based on at least one of the filtered stream of accelerometer body motion data or the filtered stream of magnetometer body motion data; and
- correct drift associated with the filtered stream of magnetometer body motion data based on at least one of the filtered stream of accelerometer body motion data or the filtered stream of gyroscope body motion data wherein an orientation of the more than one inertial sensor node is determined based on the filtered and corrected stream of accelerometer body motion data, the filtered and corrected stream of gyroscope body motion data, and the filtered and corrected stream of magnetometer body motion data over time.

10. The muscle activity recognition method of claim 9, wherein the server is configured to execute the motion tracking and visualization module further programmed to:
- map the more than one inertial sensor node to a part of the user's body based on a location of the identified muscle group of the user's body, identified via the muscle activity recognition module to, determine a raw orientation of the part of the user's body over time; and
- generate a revised orientation of the part of the user's body over time by filtering the determined raw orientation of the part of the user's body over time through a range of motion limiter to restrict the orientation of the part of the user's body to within limits of a normal human body.

11. The muscle activity recognition method of claim 10, wherein the server is configured to execute the motion tracking and visualization module further programmed to:
- animate the human-like avatar in the user interface, based on the revised orientation of the part of the user's body over time, such that the corresponding visualized body part of the human-like avatar moves to mimic actual motions of the part of the user's body to analyze motion of the part of the user's body including form.

12. The muscle activity recognition method of claim 1, wherein the at least one inertial sensor of each inertial sensor node comprises a triple axis accelerometer, a triple axis gyroscope, and a triple axis magnetometer.

13. The muscle activity recognition method of claim 1, wherein each inertial sensor node further comprises a microcontroller chip coupled to the at least one inertial sensor, and wherein the method further comprises:
- controlling, via each microcontroller chip, a sampling of the muscle vibration data by each respective inertial sensor node.

14. The muscle activity recognition method of claim 1, wherein the server is communicatively coupled to each inertial sensor node via a data aggregator, and wherein the method further comprises:
- sampling, by the data aggregator, the muscle vibration data from each inertial sensor node;
- compiling, by the data aggregator, the sampled muscle vibration data into the stream of muscle vibration data; and
- transmitting, by the data aggregator, the stream of muscle vibration data to the server.

15. The muscle activity recognition method of claim 14, wherein the transmitting comprises wirelessly transmitting the stream of muscle vibration data to the server to permit user mobility.

* * * * *